United States Patent [19]  [11] 4,444,182
Gregory  [45] Apr. 24, 1984

[54] ANAESTHETIC VAPORIZER

[75] Inventor: Raymond S. Gregory, Bingley, England

[73] Assignee: The Medishield Corporation Limited, London, England

[21] Appl. No.: 296,651

[22] Filed: Aug. 27, 1981

[30] Foreign Application Priority Data

Sep. 9, 1980 [GB] United Kingdom ................ 8029083

[51] Int. Cl.³ ............................................. A61M 17/00
[52] U.S. Cl. ...................... 128/204.14; 261/DIG. 65;
261/63; 137/38; 128/203.14; 128/203.25;
128/204.13
[58] Field of Search ...................... 128/200.11, 201.21,
128/203.13, 203.12, 204.14, 204.13,
203.19.203.25; 261/DIG. 65, 63; 137/38

[56] References Cited

U.S. PATENT DOCUMENTS 3,385,578 5/1968 Porter ................................. 261/122
3,420,232 1/1969 Bickford ..................... 261/DIG. 65
3,534,732 10/1970 Bickford .......................... 128/203.14
3,671,024 6/1972 Breiling .......................... 128/203.14
4,017,566 4/1977 Seidel .............................. 128/203.14
4,067,935 1/1978 Jones et al. ...................... 128/203.14

Primary Examiner—Henry J. Recla
Assistant Examiner—Karin Reichle
Attorney, Agent, or Firm—Roger M. Rathbun; Larry R. Cassett

[57] ABSTRACT

An anaesthetic vaporizer of the by-pass type has a sump 7 with an outlet flow path comprising a first run 27 leading upwardly, a second run 30 leading downwardly and a third run 32 leading upwardly again. A duct 23 connects the lower end of the run 30 with the lower part of the sump and in normal operation is sealed by the sump liquid. However, if the vaporizer is displaced such that the liquid flows from the sump into runs 27 or 30 of the outlet flow path the liquid inevitably drains from the duct 23. A flow path for inflowing gas is thereby opened directly to the downstream end of the run 30, preventing the over-administration of vapor from the device and removing any danger of liquid anaesthetic being blown through the device from the runs 27 and 30.

23 Claims, 8 Drawing Figures

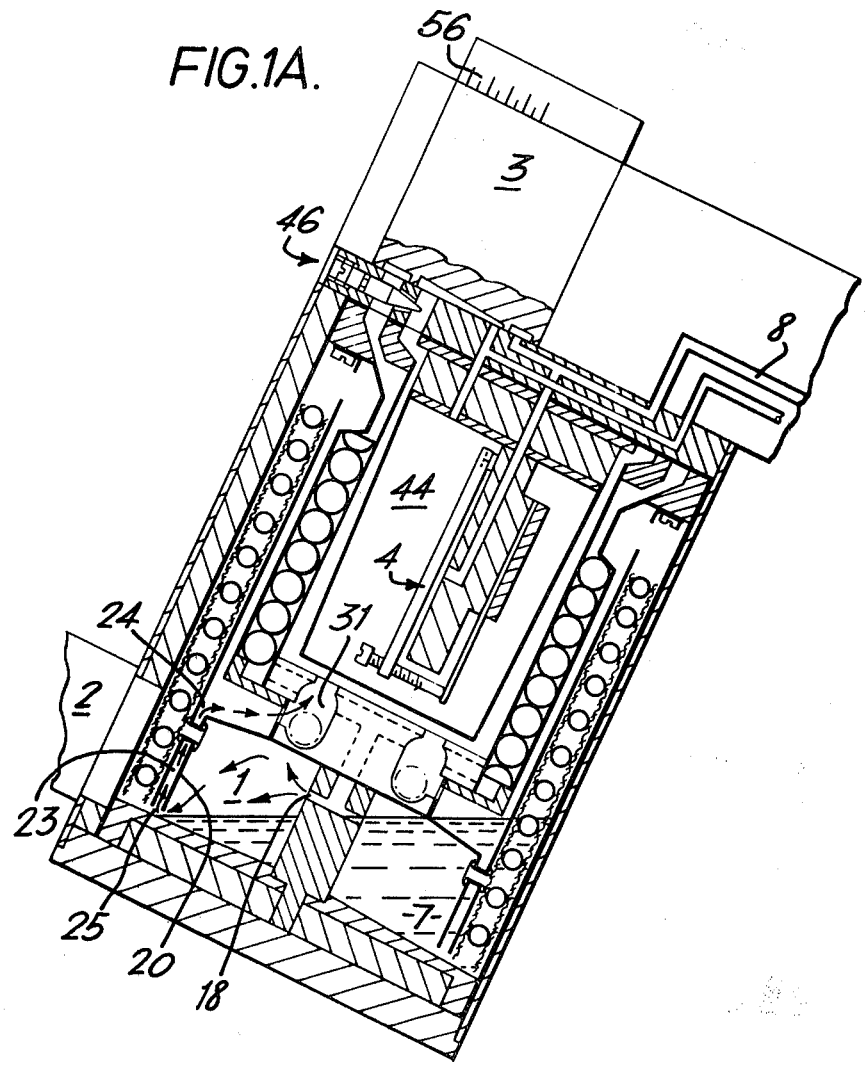

ANAESTHETIC VAPORIZER

BACKGROUND OF THE INVENTION

The present invention relates to anaesthetic vaporisers, which are devices for mixing the vapour of a volatile liquid anaesthetic agent with a supplied gas (which term is to be understood to include gas mixtures), for subsequent administration to a patient. Throughout this specification, the term 'anaesthetic' is intended to embrace both anaesthetics and analgesics.

Particularly, though not exclusively, the invention is concerned with anaesthetic vaporisers of the by-pass type wherein the gas supplied to the vaporiser is divided into two streams, the first of which passes through a vaporising chamber where the gas becomes saturated with the vapour of the volatile agent and the second of which by-passes the vaporising chamber, the two streams subsequently reuniting. The vaporising chamber usually comprises a sump for liquid anaesthetic over which the supplied gas can flow, usually also with wicks extending into the liquid and past which the gas also flows.

In normal usage this by-pass arrangement permits the concentration of anaesthetic vapour in the gas delivered from the vaporiser to be controlled to a high degree of accuracy and reliability. Specifically, this may be achieved by means of a concentration dial linked to, or forming part of, a valve which can be adjusted to control the resistance to gas flow through the vaporising chamber circuit. This has the effect of altering the proportions in which the inflowing gas is divided into the two aforementioned streams, hence altering the concentration of vapor-saturated gas in the subsequently reunited flow. Furthermore, a thermal compensation valve may be employed in the by-pass circuit by which the resistance to gas flow through that circuit can be controlled. This again affects the proportioning of the two streams and the parameters of this valve can be selected so as substantially to compensate for variations in the vapour pressure to the volatile agent (and hence its saturation concentration) with temperature.

Nevertheless, anaesthetic vaporisers even of the above-described type have their drawbacks. In this connection it is inherent in the mode of operation of an anaesthetic vaporiser that the vaporiser be used only in a specified orientation. If a conventional vaporiser is displaced from its intended orientation to a substantial degree while charged with liquid anaesthetic there is the likelihood that liquid will find its way into the gas outlet passages of the vaporiser with potentially dire results. Specifically, the hazards associated with such an occurrence may include the administration of a dangerously high concentration of anaesthetic agent as the liquid vaporises, the possible lethal delivery of liquid into a patient's airway, or (in the by-pass case) a dangerous change in the delivered concentration due to the presence of liquid in a part of the vaporiser where it is not intended to be altering the relative resistances to gas flow through the parallel circuits. There have in face been reported cases of fatalities when a free standing vaporiser has been knocked over during use and the resultant surge of liquid from the outlet of the vaporiser has been blown into the patient's airway. The tilting or inversion of a conventional, charged vaporiser even when disconnected from the gas supply is also potentially hazardous, however, and this problem is highlighted by the increasing use of anaesthesia machines which have provision for readily interchanging vaporisers, as explained below.

There are a number of different volatile anaesthetic agents having different medically desirable properties in common usage today. However, the various agents have different vapour pressure characteristics and are effective in different output concentrations, with the result that different vaporisers specifically constructed and calibrated for use with each agent are required. With the advent of anaesthesia machines with port valve fittings which permit the rapid installation and removal of different vaporisers, a given machine can readily be adapted for the administration of any one of the range of available anaesthetic agents and, using the same basic machine, the anaesthetist is accordingly given the freedom to match the correct agent as far as possible to the needs of every patient. Desirable as this practice is, it leads to an increase in the occasions when a charged vaporiser must be carried around from one station to another (e.g. from a storage rack to an anaesthesia machine or vice versa) and fitted in place at the different stations. If in the course of this handling a charged vaporiser is inadvertently inverted or tilted to a substantial degree then, even though there may be no gas flowing through it at the time, the danger exists of it subsequently delivering a higher than intended anaesthetic concentration if the liquid has been permitted to collect in any part of the gas outlet passages.

Heretofore, vaporisers have been available which have 'non-spill' properties in that if a vaporiser is tilted or inverted the contained liquid cannot reach the outlet from the vaporising chamber. Such vaporisers have employed relatively large cylindrical vaporising chambers with the gas inlet(s) and outlet(s) from the chamber being placed in the region of its centre of volume. For this 'non-spill' approach to be effective, the vaporising chambers of such devices must have internal volumes of many times the free liquid capacity and hence they are unsuitable for use in conjunction with continuous flow anaesthesia machines where they are liable to be subject to fluctuating back pressures from lung ventilators etc. It is a requirement of vaporisers intended for such use that the free volume in the vaporising chamber be as small as possible because the larger the free volume of vapour-saturated gas within the vaporiser the more likely it is that vapour can be carried back to the inlet of the vaporiser by a reverse-flowing pressure wave, despite measures which are designed to minimise the effects of such back pressures. If this back flow occurs the vapour can then flow forward through the by-pass circuit during the next pressure cycle, thereby increasing the anaesthetic concentration delivered by the vaporiser to an uncontrollable degree.

SUMMARY OF THE INVENTION

It is to the solution of these drawbacks of prior vaporisers that the invention is directed and the invention accordingly resides in an anaesthetic vaporiser comprising a chamber defining at least in part a sump for volatile liquid anaesthetic, an inlet into and an outlet from the chamber for the passage therethrough of gas, gas/-vapour, a main flow path connecting the inlet to the outlet, the main flow path including a tortuous section having a total free volume not less than the maximum volume of liquid intended to be held in the sump; and a by-pass flow path which is blocked by the presence of liquid in the sump when the vaporiser is in its intended orientation ready for use but which permits the passage of gas, gas/vapour from the inlet to the outlet of the chamber when the vaporiser is displaced substantially from its intended orientation such that liquid flows from the sump and occupies space within the tortuous section.

In one embodiment, the sump may have at least one inlet for supply gas and at least one outlet for gas/vapour, said inlet(s) and outlet(s) being located above the intended level of liquid in the sump when the vaporiser is in its intended orientation ready for use, the tortuous section for gas/vapour extending from the sump outlet(s) and having in succession a first run leading upwardly and a second run leading downwardly (such directions being expressed in the sense of flow of gas/vapour from the sump with the vaporiser in its intended orientation ready for use), the lower part of the second run being disposed at a level higher than the intended level of liquid in the sump when the vaporiser is in its intended orientation ready for use and the total free volume of said first and second runs being not less than the maximum volume of liquid intended to be held in the sump; and the by-pass flow path including at least one port opening from the lower part of the second run of said tortuous section and connecting through a duct with a second port opening to the lower part of the sump; whereby with liquid in the sump and the vaporiser disposed in its intended orientation for use, the or each such duct is sealed by such liquid but if the vaporiser is displaced substantially from said orientation such that the liquid flows from the sump into said tortuous section the or at least one such duct is open by virtue of the liquid draining therefrom.

In an alternative embodiment, the sump may have at least one inlet and at least one outlet for the passage of gas/vapour therethrough, said inlet(s) and outlet(s) being located above the intended level of liquid in the sump when the vaporiser is in its intended orientation ready for use; the tortuous section having in succession a first run leading downwardly, a second run leading upwardly and a third run leading downwardly towards the sump inlet(s), (such directions being expressed in the sense of flow of gas, gas/vapour towards the sump with the vaporiser in its intended orientation ready for use), the lower part of the second run being disposed at a level higher than the intended level of liquid in the sump when the vaporiser is in its intended orientation for use, and the total free volume of said second and third runs being not less than the maximum volume of liquid intended to be held in the sump; and the by-pass flow path including at least one port opening from the power part of the second run of said tortuous section and connecting through a duct with a second port opening to the lower part of the sump; whereby with liquid in the sump and the vaporiser disposed in its intended orientation for use the or each such duct is sealed by such liquid but if the vaporiser is displaced substantially from said orientation such that liquid flows from the sump into tortuous section the or at least one duct is opened by virtue of the liquid draining therefrom.

In yet a further embodiment, the sump may have at least one inlet and at least one outlet for the passage of gas, gas/vapour therethrough, said inlet(s) and outlet(s) being located above the intended level of liquid in the sump when the vaporiser is in its intended orientation ready for use; the tortuous section including at least a first run and a second run extending in opposite directions, the lower part of the said second run being disposed at a higher level than the intended level of liquid in the sump when the vaporiser is in its intended orientation ready for use and the total free volume of said first and second runs being not less than the maximum volume of liquid intended to be held in the sump; the by-pass flow path including at least one port opening from the lower part of the second run of said tortuous section and connecting through a duct with a second port opening into the sump, whereby with liquid in the sump and the vaporiser disposed in its intended orientation ready for use said liquid seals the by-pass flow path but if the vaporiser is displaced substantially from said orientation ready for use such that the liquid flows from the sump and occupies space within the tortuous section, gas, gas/vapour can pass from said one port via the duct through the second port towards said chamber outlet.

BRIEF DESCRIPTION OF THE DRAWINGS

Embodiments of the invention will now be described, by way of example, reference being made to the Figures of the accompanying diagrammatic drawings in which:

FIGS. 1A and 1B are schematic sectional views of the vaporiser of FIG. 1 in different orientations;

DESCRIPTION OF PREFERRED EMBODIMENTS

Figure 1:
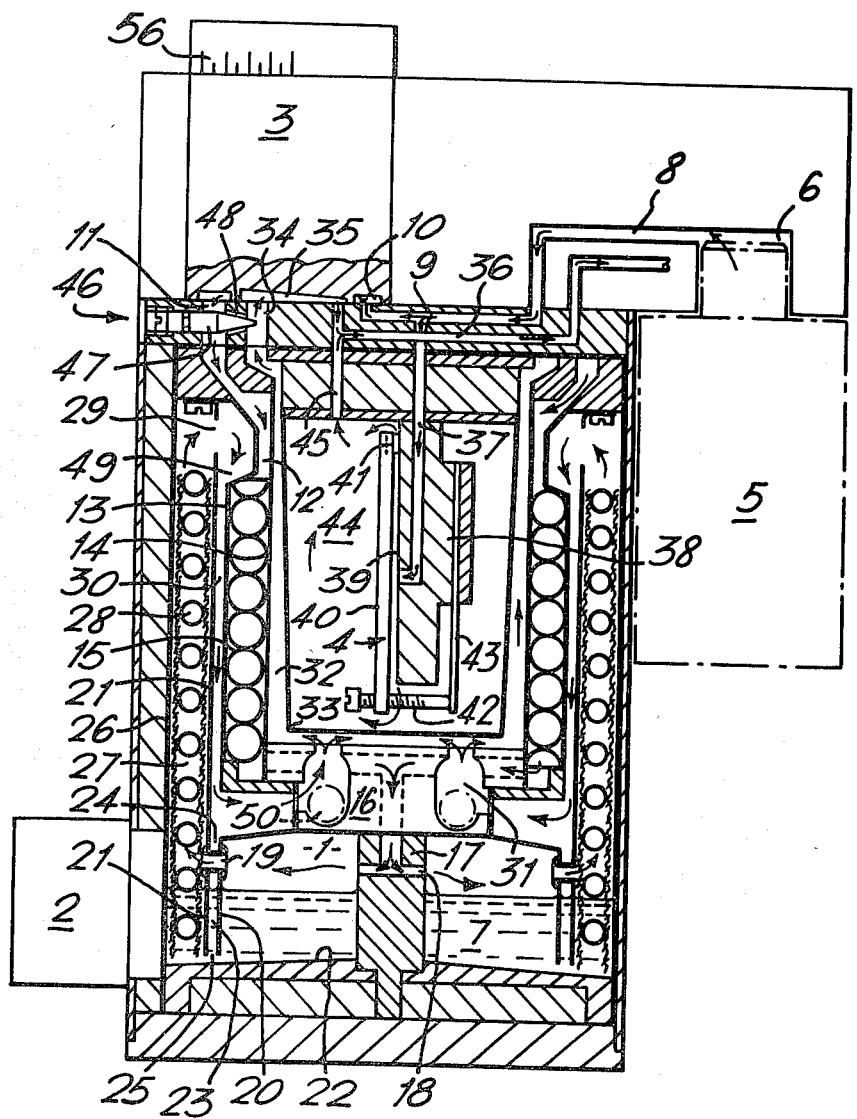
FIG. 1 is a schematic sectional view of a first anaesthetic vaporiser in its intended orientation ready for use.
Figure 1B:
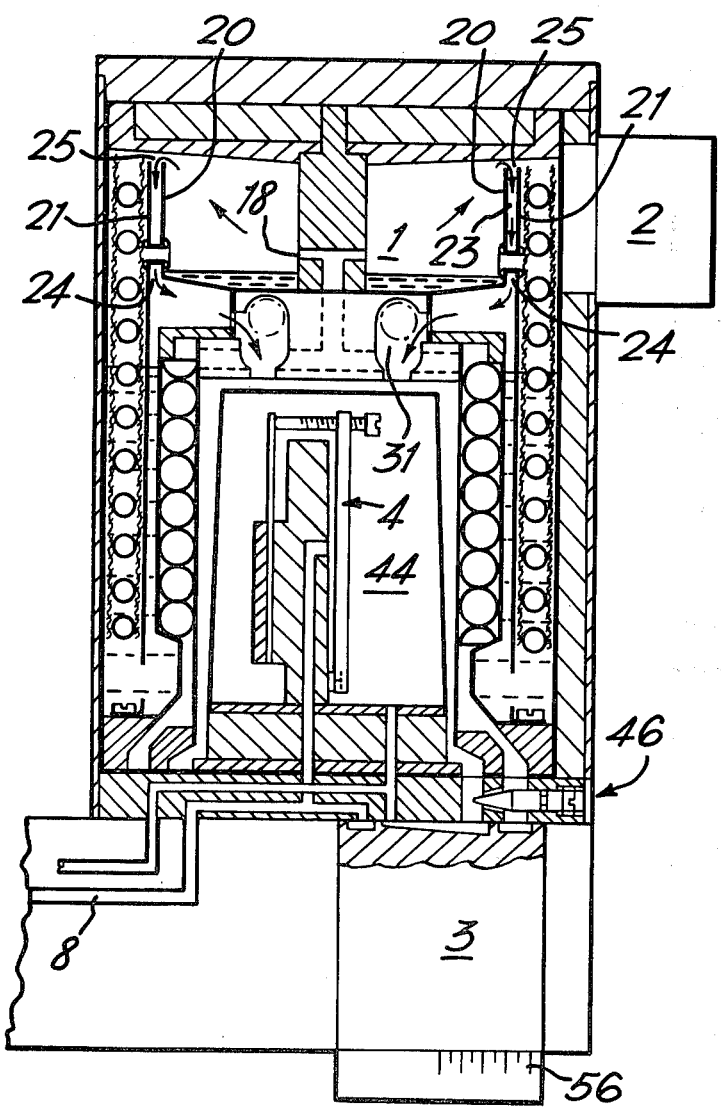

As shown in FIGS. 1, 1A and 1B, the anaesthetic vaporiser is of the by-pass type, and features a chamber 1 partly defining a sump of circular plan form for volatile liquid anaesthetic 7, a liquid filler 2, a concentration dial 3 and a thermal compensation valve 4. In this example the vaporiser is intended to be compatible with the SELECTATEC (registered trademark) mounting system as marketed by the present applicants, whereby vaporisers can be readily coupled to the back bar of an anaesthesia machine in a removable, plug-in fashion. To this end the vaporiser is provided with supplied gas inlet and gas/vapour outlet sockets designed to received valved ports upstanding from the anaesthesia machine's back bar 5. One such port and socket arangement, for the supplied gas inlet to the vaporiser, is generally indicated at 6 in FIG. 1, the port and socket for the outlet from the vaporiser being spaced laterally therefrom.

It is convenient firstly to describe the vaporiser in terms of its normal working, when supported by the back bar 5 in the upright orientation shown in FIG. 1.

It is assumed that the sump has been filled with volatile liquid anaesthetic 7 to the maximum level indicated in FIG. 1. The filler 2 is designed to set the maximum amount of liquid which can be poured into the sump, as is conventional.

Respirable gas (e.g. mixed oxygen and nitrous oxide) enters the inlet duct 8 of the vaporiser from the port/socket 6. The inflowing gas is divided into two streams at 9, a first stream to flow through the vaporising chamber 1 and a second (by-pass) stream to flow through the valve 4.

The first stream is directed through an arcuate channel 10 in the lower face of concentration dial 3 and into an inlet 11. Inlet 11 leads to an annular chamber 12 defined between two walls 13 and 14. Disposed within chamber 12 is a coiled length of open tubing 15. There is thus defined for the inflowing supplied gas a number of parallel helical pathways (one pathway through the interior of the tubing and others defined externally of the tubing between its adjacent coils) leading eventually to a central manifold block 16. The purpose of these relatively long inlet pathways is to absorb the effects of back flowing pressure waves when, e.g. a lung ventilator is used in the breathing circuit, and specifically to prevent vapour from chamber 1 being driven in the reverse direction under the action of back pressues to the extent that it could reach the duct 8 and thereafter pass through the by-pass circuit. From the manifold block 16 the inflowing gas passes into a member 17 and out through two or more outlets 18 into the chamber 1.

The gas flows over the surface of the liquid anaesthetic 7, picking up its vapour, and then leaves the chamber through a number (typically 6 or 8) of radial outlets 19 which bridge the space between a pair of annular walls 20 and 21. The walls 20, 21 extend downwardly into the liquid in the sump but terminate short of the bottom surface 22 of the sump. The walls 20, 21 therefore effectively define a vertical annular duct 23 having an upper port 24 and a lower port 25 which form part of a by-pass flow path, the purpose of which will be described hereinafter. It will be noted, however, that in normal operation of the vaporiser this duct 23 is sealed by the presence of liquid anaesthetic 7 in the sump. Moreover, the bottom surface 22 of the sump is domed as shown to ensure that the duct 23 normally remains sealed by liquid virtually so long as any unconsumed liquid remains in the sump. Alternatively an annular well could be provided in the bottom surface of the sump and into which the lower ends of the walls 20 and 21 extend.

Wall 21 continues upwardly and defines with the casing 26 of the vaporiser an annular chamber 27 in which is disposed a pair of cylindrical wicks separated by a helical coil forming a wick assembly 28 dipping into the liquid anaesthetic 7. The gas/vapour from chamber 1 passes upwardly through chamber 27, picking up further vapour from the wick assembly 28 until it is effectively saturated. Having reached the top of this chamber, the gas/vapour passes through apertures 29 in the wall 21 and then descends through an annular passage 30 defined between the walls 21 and 13. In effect, the chamber 27 and passage 30 form a tortuous section which forms part of a main flow path connecting inlet 11 to an outlet 34 from the chamber 1. It will be noted that at the lower end of passage 30 is the upper port 24 of duct 23. The gas/vapour cannot pass through this duct, however, because it is sealed by the sump liquid 7. Rather, the gas/vapour flows through ports 31 in the central manifold block 16 and into a chamber 32 defined between the manifold block 16, wall 14 and a cover member 33 for the thermal compensation valve 4. The gas/vapour flows upwardly through this chamber to the outlet 34. From here it flows through a tapering, arcuate channel 35 in the lower face of the concentration dial 3, to reunite with the gas stream from the by-pass circuit in an outlet duct 36. The outlet duct 36 leads to an outlet socket and port (not shown) on the back bar 5 similar to the inlet port/socket 6.

The second or by-pass gas stream flows from the inlet duct 8 through a duct 37 in the body 38 of the thermal compensation valve 4. This gas emerges from the duct 37 between a flat face 39 of the valve body and a plate 40 pivoted to the valve body at 41. A set screw 42 passes through the plate 40 and bears on a bimetallic strip 43. The gas passing between the face 39 and the plate 40 flows into the chamber 44 defined by the valve cover member 33, and flows thence through a duct 45 to reunite with the gas/vapour stream from vaporising chamber 1 in outlet duct 36.

In use, the concentration of anaesthetic vapour in the outlet flow from the vaporiser depends on the proportioning of the inflowing gas between the first vaporising chamber stream and the second by-pass stream. At constant temperature, the resistance to flow through the by-pass circuit remains constant and control of the proportioning between the two streams is effected by controlling the resistance to flow through the vaporising chamber circuit. This is determined by the effective size of the channel 35 at the downstream end of the vaporising chamber circuit, which can be varied by rotation of the concentration dial 3. At the same time, compensation for temperatures changes (and hence changes in the saturation concentration of the vapour in the first stream) is effected by the valve 4 changing the resistance to flow through the by-pass circuit. As the temperature varies, so the bimetallic strip 43 is effective to pivot the plate 40 towards or away from the face 39, thereby altering the effective size of the passage through which the second by-pass stream has to flow in passing from duct 37 into chamber 44.

The effect of these controls is that with a specified liquid anaesthetic agent in sump 7 the vaporiser can deliver a gas/vapour stream through duct 36 over a range of vapour concentrations corresponding to the values displayed by a suitable scale 56 on the concentration dial 3, and the set concentration will be substantially unaffected by normal temperature variations. The concentration dial also has an 'OFF' position in which the duct 9 and outlet 34 are blanked off by faces at the ends of channels 10 and 35 respectively.

The use of a concentration dial and thermal compensation valve in this manner is known. However, it will be appreciated that during the manufacture of such a vaporiser the characteristics of the dial and valve have to be selected carefully if the correct balance between the two gas streams is to be struck and if the actual output concentration from the vaporiser is to correspond with the value read on the concentration scale. With known vaporisers this frequently involves having to interchange the thermal compensation valve or to adjust the relative position between the scale markings and the tapering channel (or equivalent) on the concentration dial. Both procedures can be time-consuming and require subsequent checking. The vaporiser shown in FIG. 1, however, overcomes this problem by the incorporation of a fine adjustment valve 46 in the form of a screw threaded needle 47 which controls the flow of gas through an auxilllary by-pass passage 48 joining inlet 11 and outlet 34. As will be appreciated by opening valve 46 a proportion of the inflowing gas which would otherwise flow through the whole of the vaporising chamber circuit is allowed to by-pass the sump and rejoin the circuit on its outlet side but upstream of the channel 35. By opening this valve, therefore, the delivered anaesthetic concentration will be reduced slightly. However, because the pressure drop across the sump and fine adjustment valve 46 (i.e. between inlet 11 and outlet 34) is substantially less than the pressure drop across channel 35, the setting of the fine adjustment valve has a negligible effect upon the relative flows through the primary by-pass circuit and the vaporising chamber circuit as a whole.

In practice, the vaporiser is designed so that the delivered concentration of the vaporiser with the fine adjustment valve closed will be slightly greater than that actually desired and displayed by the scale 56. A final exact calibration can then be achieved in the factory by unscrewing the needle 47 whilst observing the delivered concentration on a suitable instrument, typically a refractometer. When the correct output is obtained the needle is locked in place and sealed to prevent user-adjustment.

Let it now be assumed that, with liquid anaesthetic in the sump, the illustrated vaporiser is displaced from its upright position (see FIGS. 1A and 1B). An advantage of the mounting system intended for the vaporiser is that such displacement cannot occur *while gas is flowing through* the unit, although such an occurrence is possible if the vaporiser is used in a free standing role, and in either case it is possible that the vaporiser may be tilted or even inverted while being carried, between uses. However, the construction of the vaporiser is such as to offer protection against displacement from the upright position whether or not the vaporiser is connected to the gas supply.

As the vaporiser is tilted, it will be appreciated that the liquid level on one side of the chamber 1 will effectively rise while the level on the other side will fall. A position will be reached where liquid flows through one or more of the outlets 19 and ports 25 (see FIG. 1A) and into one side of the annular chamber 27. An advantage of having a multiplicity of outlets 19, however, is that if some of them should be blocked by liquid in this way those diametrically opposite the blocked outlets will remain open and (if the vaporiser is on-circuit) there is no tendency for pressure to be built up in the chamber 1 such as to blow the liquid further through the outlet passages of the vaporiser. In addition, the lowering of the liquid level on the side opposite to the blocked outlets 19 means that the liquid will drain out of the duct 23 on that opposite side, thereby opening the by-pass flow path and giving a direct pathway for gas from chamber 1 to flow into the lower end of annular passage 30 and out through the manifold block 16. As a result, tilting of the vaporiser will not lead to an increase in the delivered concentration of anaesthetic vapour from the device. In fact the reverse will be true as the portion of the inflowing gas which flows through duct 23 by-passes the wick assembly 28.

In the extreme case of displacement of the vaporiser, i.e. its inversion (see FIG. 1B) substantially all of the sump liquid will flow through the port 25 and outlets 19 and collect in the chamber 27 and in the annular space 49 where the chamber 27 joins the passage 30. The volume of space 49, chamber 27 and passage 30 is chosen so that it can accommodate the maximum charge of liquid which the sump can hold. With liquid filling the whole of the circumferential extent of this space it will be appreciated that (in the absence of duct 23) the action of gas flowing through the outlets 19 and along the chamber 27 would be to force such liquid through the vaporiser towards its outlet. However, such gas flow does not occur because in this condition the whole of duct 23 has been drained of liquid and the whole of this duct is therefore available to permit gas flowing into the chamber 1 to pass directly to the downstream end of the passage 30 and out through the manifold block 16. Once again, then, there is neither any tendency for liquid to be blown out of the vaporiser nor for the delivered concentration of anaesthetic vapour to be increased over the set value, in fact the reverse being the case as the whole of the inflowing gas by-passes the liquid trapped in the chamber 27, passage 30 and space 49.

A further advantageous feature of the illustrated construction is that if the vaporiser has been upset such that liquid anaesthetic enters into any part of the chamber 27 or passage 30, immediately that the vaporiser is returned to its upright position the liquid will drain back down the chamber 27 or the passage 30 and duct 23 into the sump, and no liquid will remain in such a position that on subsequent vaporisation a higher than intended anaesthetic concentration can be dispensed. Furthermore it will be appreciated that an extremely complex series of manoeuvres would have to be performed with the vaporiser for there to be any danger of liquid anaesthetic being able to reach the ports 31 of the manifold block 16, either under gravitational flow or even with gas passing through the vaporiser.

As an optional feature of the vaporiser, loose balls 50 or other position-sensitive valve means may be incorporated in the ports 31 of the manifold block 16 such as to close those ports to all gas and vapour flow in the event of the vaporiser being displaced sufficiently from its intended orientation.

In a modified form, the width of the passage 30 and duct 23 may be increased and an additional wick assembly incorporated therein to enable, if so desired, the device to be used with liquid agents of low volatility requiring more extensive wick areas to achieve satisfactory performance. This can be arranged without restricting the ability of the duct 23 to act as part of a safety by-pass flow path in the manner described above.

The advantages of a vaporiser constructed as aforesaid are as follows.

Firstly, by judicious choice of the tortuous nature of the flow path leading from the sump, the capacity of its first and second runs and the location of the port(s) opening from the second run, the vaporiser must be put through an extremely complicated set of manoeuvres for there to be any danger of liquid passing gravitationally from the sump into the third run of the outlet flow path. Further to this, however, the arrangement is such that with the vaporiser tilted or inverted such that liquid flows out of the sump and enters the first and/or second runs of the outlet flow path, at least one of the aforesaid ducts will open to allow any inflowing gas to pass out of the sump directly into the lower (i.e. downstream) part of the second run, thereby completely by-passing the liquid trapped in the first and second runs. This is an important safety feature of the invention as it means that even if a vaporiser is upset while in use there is no danger of liquid being forced into the third run of the outlet flow path and thence to the patient under the pressure of the inlet gas supply. Of course, in normal usage the duct(s) are sealed by the sump liquid so there is no tendency for gas/vapour to be directed from the second run of the outlet flow path back into the sump. On the other hand, if a charged vaporiser is upset the duct(s) provide a path by which liquid can drain back from the second run of the outlet flow path into the sump when the device is subsequently righted.

At the same time, none of these provisions mean that the free volume of vapour-saturated gas within the vaporiser must approach anything like the values which are inherent in the previously-mentioned 'non-spill' types of vaporiser. Although the first and second runs of the outlet flow path must have the specified minimum free folume, this volume is only equivalent to the actual volume of liquid which the sump of the vaporiser is intended to accommodate, and this is many times smaller than the vaporising chamber volume of an aforementioned 'non-spill' vaporiser of equivalent liquid capacity.

Figure 2:
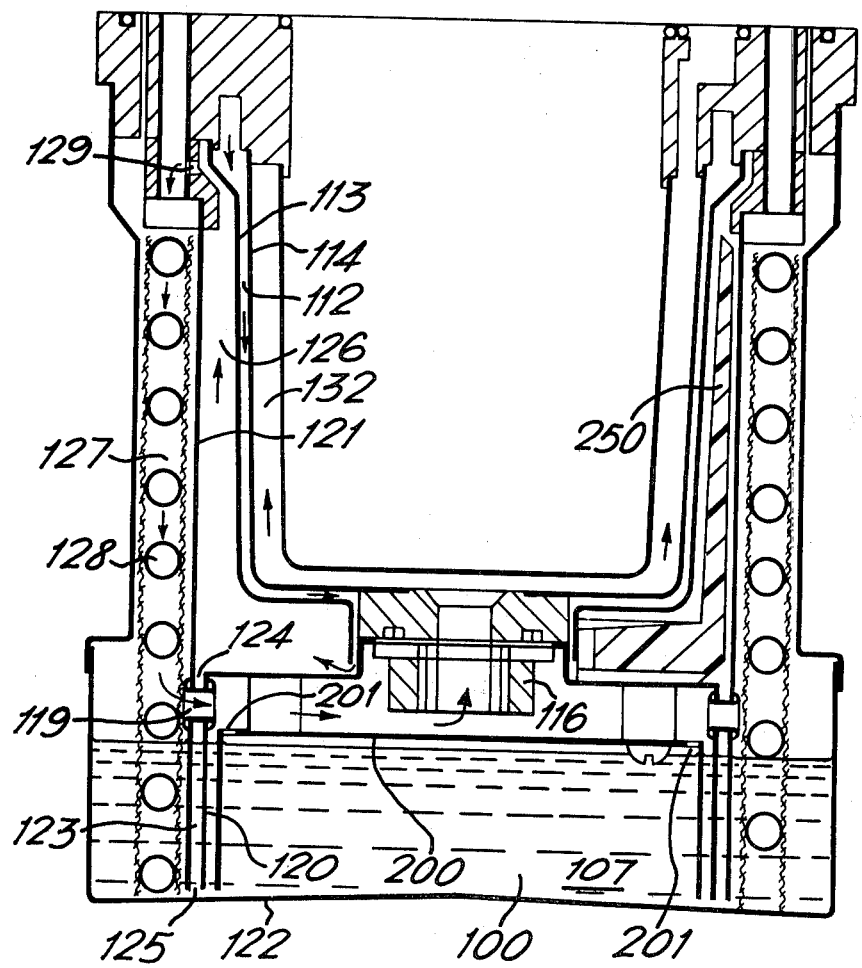
FIG. 2 is a schematic sectional view of a second anaesthetic vaporiser in its intended orientation ready for use.
Figure 2A:
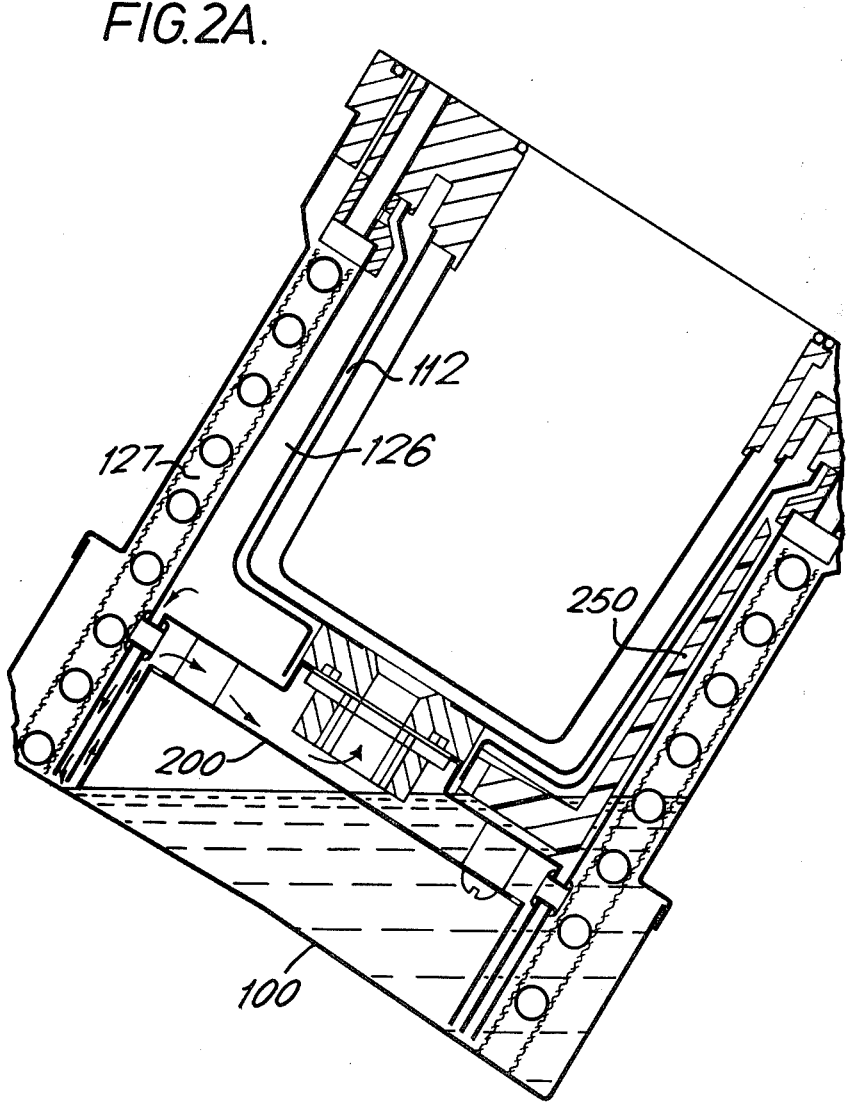
FIGS. 2A and 2B are schematic sectional views of the vaporiser of FIG. 2 in different orientations.
Figure 2B:
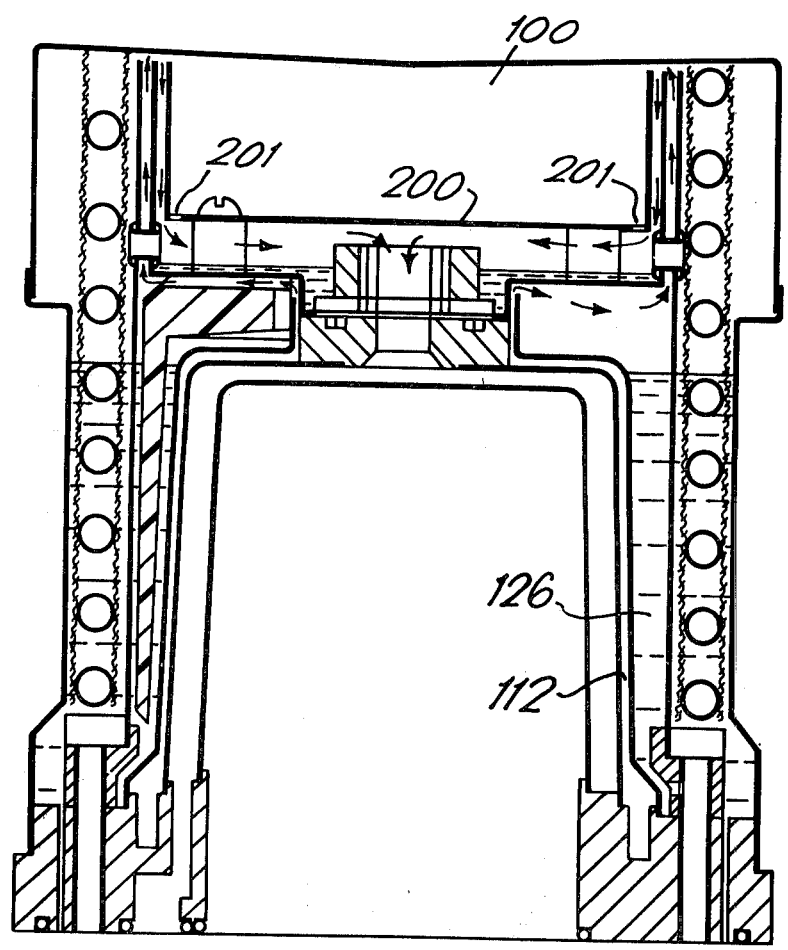

Referring now to FIGS. 2, 2A and 2B, the anaesthetic vaporiser shown is of the by-pass type and has many features not all necessarily shown, which are identical to the vaporiser of FIGS. 1, 1A and 1B. For simplicity, only those features of the vaporiser of FIGS. 2, 2A and 2B which are different from those of the vaporiser of FIGS. 1, 1A and 1B, will be referred to in detail with reference to the Figures.

As shown, the vaporiser of FIGS. 2, 2A and 2B includes a chamber 100 which defines in part a sump for volatile liquid anaesthetic 107. As with the previously described vaporiser, this vaporiser is intended to be compatible with the SELECTATEC (Registered Trademark) mounting system and includes a liquid filler, a concentration dial, a thermal expansion valve and a fine adjustment valve (none of which are shown).

For convenience, it is assumed that the sump has been filled with a volatile liquid anaesthetic 107 to the maximum level indicated in FIG. 2. Furthermore, it is assumed that the vaporiser is in its normal orientation ready for use.

Respirable supplied gas enters an inlet duct (not shown) of the vaporiser and is divided as in the earlier embodiment into two streams, a first stream as indicated by the arrows which flows through the vaporising chamber 100 and a second (bypass) stream, not indicated, which flows through a thermal compensation valve (not shown) as previously explained.

The first stream is directed to an annular chamber 112 defined between two walls, 113 and 114, where it flows downwardly (as shown in FIG. 2) until it reaches the lowermost part of the chamber 112. The first stream of supplied gas then flows upwardly between the wall 113 and a further wall 121 which define between them a second annular chamber 126. Adjacent the top of the second chamber are apertures 129 (only one shown) through which the supplied gas passes to flow downwardly once again through a chamber 127. The chamber 127 contains a wick assembly 128 which dips into the liquid 107 and by its passage through the chamber 127 the supplied gas entrains vapour from the volatile liquid soaked up by the wick assembly 128.

In other words, the chambers 112, 126 and 127 constitute a tortuous section of a flow path for the supplied gas, which tortuous section in succession comprises a first run leading downwardly, a second run leading upwardly and a third run leading downwardly towards the sump.

The total free volume of the chambers 126, 127, that is, the second and third runs is not less than the maximum volume of liquid 107 intended to be held in the sump.

The supplied gas/vapour when it reaches the bottom of the chamber 127 passes through at least one inlet 119 towards a central manifold block 116. The gas/vapour then passes through the manifold block 116 into an annular chamber 132 and joins the second (by-pass) stream of supplied gas in a manner similar to that heretofore described with reference to the first embodiment.

The inlets 119 are arranged above the level of the volatile liquid 107 as shown in FIG. 2. As with the previous embodiment the inlets 119 bridge the space between a pair of annular walls 120, 121. These walls extend downwardly into the liquid in the sump but terminate short of its bottom 122. The walls 120, 121 therefore effectively define a vertical annular duct 123 having an upper port 124 and a lower port 125 which form part of a by-pass flow path, the purpose of which will be described hereinafter. It is illustrated in FIG. 2 that in normal operation of the vaporiser, duct 123 is sealed by the presence of liquid anaesthetic 107 in the sump. Moreover, the bottom surface 122 of the sump is domed as shown to ensure that the duct 123 normally remains sealed by liquid virtually so long as any unconsumed liquid remains in the sump.

As with the previous embodiment an annular well could be provided in the bottom surface of the sump and into which the lower ends of the walls 120, 121 could extend.

Within the wall 120 is a baffle 200 in the form of an inverted dish. At the base of the dish around its periphery there are provided a plurality of holes 201.

Let it now be assumed that with liquid anaesthetic in the sump the vaporiser of FIG. 2 is displaced from its upright position as per FIG. 2A. As the vaporiser is tilted it will be appreciated that the liquid level on one side of the chamber 100 will effectively rise while the level on the other side will fall. A position will be reached where liquid flows through one or more of the inlets 119 and into one side of the annular chamber 127. The liquid will be guided towards the chamber 127 by the baffle 200 and in particular by the holes 201.

As explained in the previous embodiment, an advantage of having a multiplicity of inlets 119 is that if some of them should be blocked by liquid, those diametrically opposite the blocked inlets will remain open and (if the vaporiser is on circuit) there is no tendency for pressure to be built up such as to blow the liquid towards the outlet passages of the vaporiser. In addition, the lowering of the liquid level on the side opposite to the blocked inlets 119 means that the liquid will drain out of the duct 123 on that opposite side, thereby opening the by-pass flow path and giving a direct path for the supplied gas through the port 124, duct 123, port 125 between the wall 120 and the baffle 200 towards the manifold block 116. As a result, tilting of the vaporiser will not lead to an increase in the delivered concentration of anaesthetic vapour from the device.

In the extreme case of displacement of the vaporiser, that is, its inversion, (see FIG. 2B) substantially all of the sump liquid will flow through the holes 201 and the inlets 119 and collect in the chambers 127 and 126.

As previously explained the volume of the chambers 127, 126 is chosen so that it can accommodate the maximum charge of liquid which the sump can hold. With the liquid filling the whole of the circumferential extent of chambers 127, 126 it will be appreciated that in the absence of duct 123 the action of gas flowing through the chamber 112 and towards the chamber 126 would be to force such liquid through the vaporiser towards its outlet. However, such gas flow does not occur because in this condition the whole of duct 123 has been drained of liquid and the whole of this duct is therefore available to permit gas flowing from the chamber 112 to pass unhindered towards the manifold block 116.

Minor amendments can be made as per the plastics filler 250 which occupies some of the space in chamber 126. The volume of the plastics filler can be altered to vary the capacity of the chamber 126.

Figure 3:
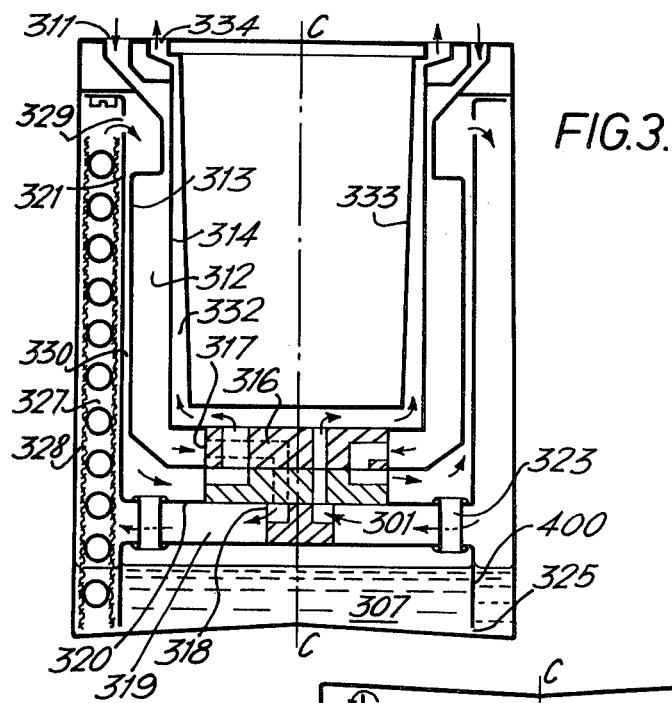
FIG. 3 is a schematic sectional view of a third anaesthetic vaporiser in its intended orientation ready for use and illustrating alternative flow paths for supply gas, gas/vapour.
Figure 3A:
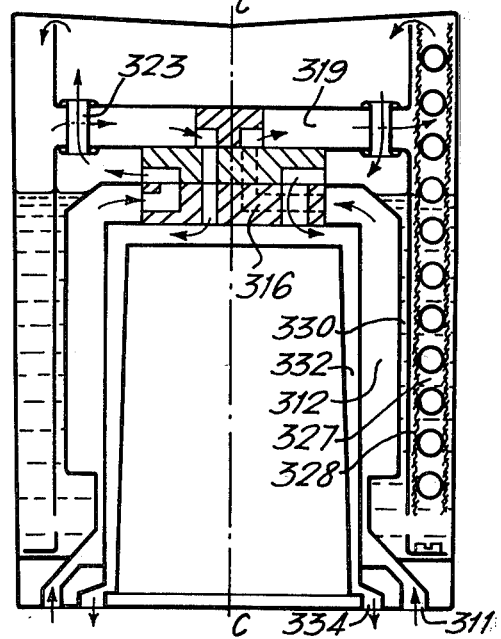
FIG. 3A is a schematic sectional view of the vaporiser of FIG. 3 inverted.

Referring now to FIGS. 3 and 3A which illustrate yet a further embodiment of an anaesthetic vaporiser of the by-pass type. Again, this vaporiser has many features not all necessarily shown which features are identical to the vaporiser of FIGS. 1, 1A and 1B. For simplicity, only those features of the vaporiser of FIGS. 3, 3A which are different from those of the vaporiser of FIGS. 1, 1A and 1B will be referred to in detail with reference to the Figures.

As with the previously described vaporiser, this vaporiser is intended to be compatible with the SELECTATEC (registered trademark) mounting system and includes a liquid filler, a concentration dial, a thermal expansion valve and a fine adjustment valve (none of which are shown).

For convenience, it is assumed that the sump has been filled with a volatile liquid anaesthetic 307 to the maximum level indicated in FIG. 3. Furthermore, it is assumed that the vaporiser is in its normal orientation ready for use as shown in FIG. 3.

Respirable supplied gas enters an inlet duct (not shown) of the vaporiser and is divided as in the earlier embodiments into two streams, a first stream as indicate by the arrows which flows through the vaporising chamber 301 and a second (by-pass) stream, not indicated, which flows through a thermal expansion valve (not shown) as previously explained.

As is shown in FIG. 3, with a manifold block 316 arranged centrally within the chamber 301 the flow of gas, gas/vapour through the chamber 301 can be arranged differently according to the arrows on the left-hand or right-hand side of the centre line C—C. Referring first to the left-hand side of the centre line C—C, supplied gas enters the chamber 301 via an inlet 311 and flows downwardly towards manifold block 316 through an annular chamber 312 defined between walls 313 and 314. The chamber 312 may include tubing as described in the first embodiment.

The inflowing supplied gas enters the manifold block 316 at manifold inlets 317 and leaves the manifold block 316 via manifold outlets 318. The supplied gas flows along a passageway 319 defined by a wall 320 and the upper surface of an inverted dish-shaped baffle 400. The peripheral edge of the baffle 400 stops short of the floor of the sump and defines with the floor of the sump a port 325.

A plurality of ducts 323 bridge the passageway 319 and permit communication between the sump and in particular the space enclosed by the baffle 400 and a passage 330. The gas flows around the ducts 323 and into an annular chamber 327 in which is disposed a wick assembly 328. The gas passes up the chamber 327 picking up vapour from the wick assembly 328 until it reaches the top of the chamber 327 where it passes through apertures 329 in a wall 321 which defines with the wall 313 the annular passage 330. Under normal operating conditions, the gas/vapour passes down the passage 330 into the manifold block 316 and leaves the chamber 301 via outlet 334 after passage through a chamber 332. The passage 332 is defined by the wall 314 and a cover member 333.

The gas/vapour stream then joins with the second or by-pass gas stream as described with reference to FIGS. 1, 1A and 1B. In effect, the chamber 327 and passage 330 form a tortuous section of the main flow path from the inlet 311 to the outlet 334 of the chamber 301.

Should the vaporiser become inverted (see FIG. 3A), liquid would flow from the sump through the ducts 323 and the port 325 and into the passage 330 and chamber 327. This liquid would act as a barrier to gas flowing through the passageway 319 in normal usage and into chamber 327. However, gas so impeded can now flow upwardly (as shown in FIG. 3A) through chamber 327, through duct 325 and through ducts 323 to reach the manifold 316.

As previously explained, the volume of the chamber 327 and passage 330 is chosen so that it can accommodate the maximum charge of liquid which the sump can hold. With the liquid filling the whole of the circumferential extent of chambers 327 and passage 330 it will be appreciated that in the absence of a by-pass flow path formed in part by the ducts 323 the action of gas flowing through the chamber 327 would be to force such liquid through the vaporiser towards its outlet. This, of course, does not happen because when the liquid in the sump flows outwardly therefrom and into the chamber 327 and passage 330 it opens up the by-pass flow path.

Referring briefly to the passage of gas on the right-hand side of the centre line C—C, gas enters the inlet 311 and flows down the chamber 312 and hence into the passage 330. The supplied gas then flows up the passage 330 through the apertures 329 and into the chamber 327 occupied by the wick assembly 328. The gas flows down the chamber 327 and entrains vapour and enters the passageway 319 flowing around the ducts 323 and into the manifold block 326. The gas/vapour then flows out from the manifold block 316 into the chamber 332 and hence out of the chamber 301 via the gas/vapour outlet 334.

If this gas flow arrangement is used, then again on inversion of the vaporiser when liquid anaesthetic occupies the chamber 327 and passage 330, gas will be able to flow from the passage 330 through the ducts 323 and duct 325 and hence into the passageway 319 and through the manifold 316.

Thus, the effect of providing a by-pass flow path will be the same regardless of the general flow pattern of gas, gas/vapour through the chamber 301.

I claim:

1. An anaesthetic vaporiser comprising a chamber defining at least in part a sump for volatile liquid anaesthetic, an inlet into and an outlet from the chamber for the passage therethrough of gas, gas/vapour, a main flow path connecting the inlet to the outlet with said inlet in fluid communication with said sump, the main flow path including a tortuous section having a total free volume not less than the maximum volume of liquid intended to be held in the sump; and a by-pass flow path means communicating with said main flow path, for fluidically bypassing said tortuous section said by-pass flow path means extending into said sump and defining a duct having a first port means which is blocked by the presence of liquid in the sump when the vaporiser is in its intended upright orientation ready for use, said first port means positioned to be unblocked to permit the passage of gas, gas/vapour from the inlet to the outlet through said by-pass flow path means when the vaporiser is displaced substantially from its intended upright orientation such that liquid flows from the sump and occupies space within the tortuous section.

2. An anaesthetic vaporiser as claimed in claim 1, in which the sump fluidically communicates with said main flow path through at least one sump inlet for supply gas and at least one sump outlet for gas/vapour, said sump inlet(s) and outlet(s) being located above the intended level of liquid in the sump when the vaporiser is in its intended upright orientation ready for use, the tortuous section in said main flow path receiving gas/vapour from the sump outlet(s) and having in succession a first run leading upwardly and a second run leading downwardly (such directions being expressed in the sense of flow of gas/vapour from the sump with the vaporiser in its intended upright orientation ready for use), the lower part of the second run being disposed in said sump at a level higher than the intended level of liquid in the sump when the vaporiser is in its intended upright orientation ready for use and the total free volume of said first and second runs being not less than the maximum volume of liquid intended to be held in the sump; and the by-pass flow path means including a second port means located in the lower part of the second run of said tortuous section and fluidically connected through said duct with said first port means which is located in the lower part of the sump; whereby with liquid in the sump and the vaporiser disposed in its intended upright orientation for use, the first port means is sealed by such liquid, but if the vaporiser is displaced substantially from said upright orientation such that the liquid flows from the sump into said tortuous section, the first port means is opened by virtue of the liquid draining therefrom.

3. A vaporiser as claimed in claim 2, in which said sump is of circular plan form, and a pair of coaxial, annular walls connected to the lower part of said second run at said second port means and extending axially into the sump, said pair of coaxial annular walls defining a space therebetween constituting said duct.

4. A vaporiser as claimed in claim 3, in which the outer one of said pair of annular walls extends upwardly from said sump and defines with the outside wall of the chamber an annular space constituting the first run of said tortuous section of said main flow path, and said at least one sump outlet comprising a passage means for fluidically communicating said sump and said main flow path by bridging the space between said pair of annular walls.

5. A vaporiser as claimed in claim 4, in which the chamber includes a further interior annular wall disposed above said sump, said further interior annular wall and the outer one of said pair of annular walls defining an annular space constituting the second run of said tortuous section of said main flow path.

6. A vaporiser as claimed in claim 3, in which said pair of annular walls terminate just short of the lower surface of the sump to define between them said first port means.

7. A vaporiser as claimed in claim 3, in which said pair of annular walls are disposed towards the outer margin of the sump, and the lower surface of the sump is domed to ensure that said first port means of said duct is sealed by liquid virtually so long as any liquid is present in the sump.

8. A vaporiser as claimed in claim 3, in which an annular well is provided in the lower surface of the sump and said pair of annular walls extend into said annular well thereby to ensure that said duct is sealed by liquid virtually so long as any liquid is present in the sump.

9. A vaporiser as claimed in claim 2, in which the first run of said tortuous section of said main flow path contains a wick assembly and the lower end of said wick assembly contacts the liquid within the sump.

10. A vaporiser as claimed in claim 2, in which the second run of said tortuous section of said main flow path and said duct together contain a further wick assembly and the lower end of said further wick assembly contacts the liquid within the sump.

11. An anaesthetic vaporiser as claimed in claim 1, in which the sump fluidically communicates with said main flow path through at least one sump inlet for supply gas and at least one sump outlet for gas/vapour, said sump inlet(s) and outlet(s) being located above the intended level of liquid in the sump when the vaporiser is in its intended upright orientation ready for use; the tortuous section in said main flow path having in succession a first run leading downwardly, a second run leading upwardly and a third run leading downwardly towards the sump inlet(s), (such directions being expressed in the sense of flow of gas, gas/vapour towards the sump with the vaporiser in its intended upright orientation ready for use), the lower part of the second run being disposed within the sump but at a level higher than the intended level of liquid in the sump when the vaporiser is in its intended upright orientation for use, and the total free volume of said second and third runs being not less than the maximum volume of liquid intended to be held in the sump; and the by-pass flow path means including a second port means located in the lower part of the second run of said tortuous section and fluidically connected through said duct with said first port means which is located in the lower part of the sump; whereby with liquid in the sump and the vaporiser disposed in its intended upright orientation for use, the first port means is sealed by such liquid, but if the vaporiser is displaced substantially from said upright orientation such that liquid flows from the sump through a sump inlet into said tortuous section, the first port means is opened by virtue of the liquid draining therefrom.

12. A vaporiser as claimed in claim 11, in which said sump is of circular plan form, and a pair of coaxial, annular walls connected to the lower part of said second run at said second port means and extending axially into the sump, said pair of coaxial annular walls defining a space therebetween constituting said duct.

13. A vaporiser as claimed in claim 12, in which the outer one of said pair of annular walls extends upwardly from said sump and defines with the outside wall of the chamber an annular space constituting the third run of said tortuous section of said main flow path, and said at least one sump inlet comprising a passage means for fluidically communicating said third run of the tortuous section of said main flow path and the sump by bridging the space between said pair of annular walls.

14. A vaporiser as claimed in claim 13, in which the chamber includes a further interior annular wall disposed above said sump, said further interior annular wall and the outer one of said pair of annular walls defining an annular space constituting the second run of the tortuous section of said main flow path.

15. A vaporiser according to claim 12, in which said pair of annular walls terminates just short of the lower surface of the sump to define between them said first port means.

16. A vaporiser as claimed in claim 12, wherein said pair of annular walls are disposed towards the outer margin of the sump, and the lower surface of the sump is domed to ensure that said first port means of said duct is sealed by liquid virtually so long as any liquid is present in the sump.

17. A vaporiser as claimed in claim 12, in which an annular well is provided in the lower surface of the sump and said pair of annular walls extend into said annular well thereby to ensure that said duct is sealed by liquid virtually so long as any liquid is present in the sump.

18. A vaporiser as claimed in claim 12, in which the third run of said tortuous section of said main flow path contains a wick assembly and the lower end of said wick assembly contacts the liquid within the sump.

19. A vaporiser as claimed in claim 12, in which the sump contains a baffle, the baffle having at least one hole which, when the vaporiser is in its intended upright orientation ready for use, is located above the level of liquid in the sump so that if the vaporiser is displaced substantially from said upright orientation the liquid in the sump flows through the at least one hole which directs the liquid towards the sump inlet and thence into the second and third runs of the tortuous section.

20. An anaesthetic vaporiser as claimed in claim 1, in which the sump fluidically communicates with said main flow path through at least one sump inlet for supply gas and at least one sump outlet for gas, gas/vapour, said sump inlet(s) and outlet(s) being located above the intended level of liquid in the sump when the the vaporiser is in its intended upright orientation ready for use; the tortuous section of said main flow path including at least successive first and second runs extending in opposite flow directions, the lower part of said second run being disposed within the sump but at a higher level than the intended level of liquid in the sump when the vaporiser is in its intended upright orientation ready for use and the total free volume of said first and second runs being not less than the maximum volume of liquid intended to be held in the sump; the by-pass flow path means including a second port means located in the lower part of the second run of said tortuous section and fluidically connected through said duct with the first port means 1 which is located in the sump, whereby with liquid in the sump and the vaporiser disposed in its intended upright orientation ready for use, said liquid seals the by-pass flow path means but if the vaporiser is displaced substantially from said upright orientation ready for use such that the liquid flows from the sump and occupies space within the tortuous section, gas, gas/vapour can pass from said first port means via the duct towards said outlet from said chamber.

21. A vaporiser as claimed in claim 20 being of the by-pass type.

22. A vaporiser as claimed in claim 21, comprising a valved passage means paralleling the main flow path and fluidically interconnecting a point in the main flow path upstream of the sump with a point in the main flow path downstream of the sump but upstream of said valve for enabling a selectable proportion of the gas directed through the main flow path to bypass the sump.

23. A vaporiser as claimed in claim 21 or claim 22, in which the valved passage means includes a valve means for compensating for changes in saturation concentration of a specified volatile liquid anaesthetic with changes in temperature.

* * * * *